(12) United States Patent
Arie et al.

(10) Patent No.: US 11,275,083 B2
(45) Date of Patent: Mar. 15, 2022

(54) METHOD AND SYSTEM FOR DETECTING A TARGET WITHIN A POPULATION OF MOLECULES

(71) Applicant: Ramot at Tel-Aviv University Ltd., Tel-Aviv (IL)

(72) Inventors: Ady Arie, Herzlia (IL); Amos Danielli, Moshav Hadar-Am (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 319 days.

(21) Appl. No.: 16/240,839

(22) Filed: Jan. 7, 2019

(65) Prior Publication Data
US 2019/0137504 A1 May 9, 2019

Related U.S. Application Data

(63) Continuation of application No. 15/420,159, filed on Jan. 31, 2017, now Pat. No. 10,175,246, which is a
(Continued)

(51) Int. Cl.
*G01N 33/543* (2006.01)
*G01N 21/17* (2006.01)
(Continued)

(52) U.S. Cl.
CPC ..... *G01N 33/54333* (2013.01); *C12Q 1/6818* (2013.01); *G01N 21/1717* (2013.01);
(Continued)

(58) Field of Classification Search
CPC ......... G01N 21/6428; G01N 33/54326; G01N 33/54333; G01N 2021/6439;
(Continued)

(56) References Cited

U.S. PATENT DOCUMENTS 6,280,618 B2   8/2001   Watkins et al.
6,309,701 B1 * 10/2001   Barbera-Guillem ..... B82Y 5/00
                                                        257/614
(Continued)

FOREIGN PATENT DOCUMENTS

EP      0476556       3/1992
WO      WO 99/34195   7/1999
(Continued)

OTHER PUBLICATIONS

Advisory Action Before the Filing of An Appeal Brief dated Sep. 18, 2015 From the U.S. Patent and Trademark Office Re. U.S. Appl. No. 13/909,109.
(Continued)

*Primary Examiner* — Melanie Brown

(57) ABSTRACT

A method of detecting a target within a population of molecules comprising: contacting a plurality of labeled probe molecules with the population of molecules potentially containing a target of the probe molecules; acquiring a probe specific signal emitted by said labeled probe molecules that bound to said target together with a background signal; preferentially modulating said probe specific signal by at least one of modulating said acquisition and modulating an emission of said probe specific signal; and detecting said probe specific signal over said background signal using said preferential modulation.

18 Claims, 9 Drawing Sheets

Related U.S. Application Data continuation of application No. 13/909,109, filed on Jun. 4, 2013, now Pat. No. 9,575,068, which is a continuation of application No. 12/312,071, filed as application No. PCT/IL2007/001287 on Oct. 25, 2007, now Pat. No. 8,465,989.

(60) Provisional application No. 60/854,722, filed on Oct. 27, 2006.

(51) Int. Cl.
  *G01N 21/64* (2006.01)
  *G01N 33/58* (2006.01)
  *C12Q 1/6818* (2018.01)

(52) U.S. Cl.
  CPC .......... *G01N 21/64* (2013.01); *G01N 21/6428* (2013.01); *G01N 33/54326* (2013.01); *G01N 33/54353* (2013.01); *G01N 33/582* (2013.01); *G01N 2021/6439* (2013.01)

(58) Field of Classification Search
  CPC .............. G01N 21/1717; G01N 21/64; G01N 33/54353; G01N 33/582; C12Q 1/6818
  See application file for complete search history.

(56) References Cited

U.S. PATENT DOCUMENTS

| | | | |
|---|---|---|---|
| 6,596,076 B1 | 7/2003 | Wakayama | |
| 6,760,105 B2 | 7/2004 | Oshida et al. | |
| 6,771,367 B2 | 8/2004 | Luryi et al. | |
| 8,465,989 B2 | 6/2013 | Arie et al. | |
| 9,575,068 B2 | 2/2017 | Arie et al. | |
| 2003/0003464 A1* | 1/2003 | Phan ................ | G01N 33/54366 435/5 |
| 2003/0012693 A1 | 1/2003 | Otillar et al. | |
| 2004/0018495 A1* | 1/2004 | Li .................... | C12Q 2563/149 435/6.1 |
| 2004/0043507 A1* | 3/2004 | Song ................. | B01L 3/502761 436/514 |
| 2004/0058458 A1 | 3/2004 | Anker et al. | |
| 2005/0214931 A1 | 9/2005 | Kuo et al. | |
| 2005/0284817 A1 | 12/2005 | Fernandez et al. | |
| 2006/0008924 A1* | 1/2006 | Anker .................... | G01N 33/58 436/526 |
| 2006/0205093 A1 | 9/2006 | Prins | |
| 2010/0041166 A1 | 2/2010 | Arie et al. | |
| 2013/0274137 A1 | 10/2013 | Arie et al. | |
| 2017/0138952 A1 | 5/2017 | Arie et al. | |

FOREIGN PATENT DOCUMENTS

| | | |
|---|---|---|
| WO | WO 03/043402 | 5/2003 |
| WO | WO 2008/050335 | 5/2008 |

OTHER PUBLICATIONS

Communication Pursuant to Article 94(3) EPC dated Nov. 5, 2013 From the European Patent Office Re. Application No. 07827261.4.
Communication Pursuant to Article 94(3) EPC dated Feb. 1, 2018 From the European Patent Office Re. Application No. 15201074.0. (7 Pages).
Communication Pursuant to Article 94(3) EPC dated May 26, 2010 From the European Patent Office Re. Application No. 07827261.4.
Communication Pursuant to Article 94(3) EPC dated Nov. 30, 2011 From the European Patent Office Re. Application No. 07827261.4.
Communication Relating to the Results of the International Search dated Mar. 10, 2008 From the International Searching Authority Re.: Application No. PCT/IL2007/001287.
Decision to Refuse A European Patent Application dated Oct. 20, 2015 From the European Patent Office Re. Application No. 07827261.4.
European Search Report and the European Search Opinion dated May 31, 2016 From the European Patent Office Re. Application No. 15201074.0.
International Preliminary Report on Patentability dated May 7, 2009 From the International Bureau of WIPO Re. Application No. PCT/IL2007/001287.
International Search Report dated May 20, 2008 From the International Searching Authority Re. Application No. PCT/IL2007/001287.
Notice of Allowance dated Feb. 14, 2013 From the U.S. Patent and Trademark Office Re. U.S. Appl. No. 12/312,071.
Notice Of Allowance dated Aug. 30, 2018 From the U.S. Patent and Trademark Office Re. U.S. Appl. No. 15/420,159. (8 pages).
Official Action dated Dec. 2, 2014 From the U.S. Patent and Trademark Office Re. U.S. Appl. No. 13/909,109.
Official Action dated Apr. 6, 2016 From the U.S. Patent and Trademark Office Re. U.S. Appl. No. 13/909,109.
Official Action dated Apr. 14, 2015 From the U.S. Patent and Trademark Office Re. U.S. Appl. No. 13/909,109.
Official Action dated Mar. 19, 2018 From the U.S. Patent and Trademark Office Re. U.S. Appl. No. 15/420,159. (22 pages).
Official Action dated Oct. 19, 2011 From the U.S. Patent and Trademark Office Re. U.S. Appl. No. 12/312,071.
Official Action dated Apr. 24, 2012 From the U.S. Patent and Trademark Office Re. U.S. Appl. No. 12/312,071.
Summons to Attend Oral Proceedings Pursuant to Rule 115(1) EPC Dated Apr. 23, 2015 From the European Patent Office Re. Application No. 07827261.4.
Written Opinion dated May 20, 2008 From the International Searching Authority Re. Application No. PCT/IL2007/001287.
Anker et al. "Aspherical Magnetically Modulated Optical Nanoprobes (MagMOONs)", Journal of Applied Physics, 93(10): 6698-9700, May 15, 2003.
Anker et al. "Magnetically Modulated Optical Nanoprobes", Applied Physics Letters, XP012034812, 82(7): 1102-1104, Feb. 17, 2003.
Anker et al. "Magnetically-Modulated Optical Nanoprobes (MagMOONs) and Systems", Journal of Magnetism and Magnetic Materials, 293(1): 655-662, Available Online Mar. 2, 2005.
Behrend et al. "Brownian Modulated Optical Nanoprobes", Applied Physics Letters, 84(1): 154-156, Jan. 5, 2004.
Castro et al. "Single-Molecule Detection of Specific Nucleic Acid Sequences in Unamplified Genomic DNA", Analytical Chemistry, 69(19): 3915-3920, Oct. 1, 1997.
Wabuyele et al. "Approaching Real-time Molecualr Diagnostics: Single-Pair Fluorescence Resonance Energy Transfer (spFRET) Detection for the Analysis of Low Abundant Point Mutations in K-Ras Oncogenes", Journal of the American Chemical Society, JACS, 125: 6937-6945, 2003.
Wikipedia "Wiki p. Induction", Wikipedia, The Free Encyclopedia, XP055012894, p. 1-10, Nov. 23, 2011.

\* cited by examiner

METHOD AND SYSTEM FOR DETECTING A TARGET WITHIN A POPULATION OF MOLECULES

RELATED APPLICATIONS

This application is a continuation of U.S. patent application Ser. No. 15/420,159 filed on Jan. 31, 2017, which is a continuation of U.S. patent application Ser. No. 13/909,109 filed on Jun. 4, 2013, now U.S. Pat. No. 9,575,068, which is a continuation of U.S. patent application Ser. No. 12/312,071 filed on Apr. 24, 2009, now U.S. Pat. No. 8,465,989, which is a National Phase of PCT Patent Application No. PCT/IL2007/001287 having International Filing Date of Oct. 25, 2007, which claims the benefit of priority of U.S. Provisional Patent Application No. 60/854,722 filed on Oct. 27, 2006. The contents of the above applications are all incorporated by reference as if fully set forth herein in their entirety.

FIELD AND BACKGROUND OF THE INVENTION

The present invention relates to detecting a target within a population of molecules, and more specifically, but not exclusively, to rapid detection of a non-amplified target.

INTRODUCTION

Detection of a target present at a low concentration and/or at a low number in a population of molecules is a well known challenge in many biological applications.

Bioanalytical systems generally consist of a biosensor and a detection system. The biosensor couples a biological recognition element (e.g., a labeled probe, or a peptide) with specificity to a selected target and a physical transducer (e.g., a fluorescent source, a metal nano-particle or a radio-isotope) that can produce a signal when the biological recognition element binds to the selected target. The detection system is designed in consideration of the physical transducer employed (e.g., an optical system detects the fluorescent signal and a scintillation counter is used to detect a radioisotope).

Previously available approaches which do not amplify the target, include, but are not limited to blotting (e.g. Southern, northern and western blotting), immuno-precipitation, in-situ hybridization (e.g. fluorescent in situ hybridization; FISH) and fluorescent activated cell sorting (FACS).

One previously known approach to detection of specific DNA sequences uses fluorescent dyes as the physical transducer and direct detection of the light emitted from the biological sample. Since direct detection of the fluorescent light is relatively insensitive, a pre-amplification phase is often employed (e.g., Rolling circle amplification, Serial invasive signal amplification reaction). The optical detection is done by gel electrophoresis or spectrofluorometer. Amplification times associated with these techniques typically exceed 1 hour.

A second previously known approach to detection of specific DNA sequences also uses fluorescent dyes as the physical transducer. However, the optical detection is done in the time domain. Popular techniques in this category is Fluorescence Correlation Spectroscopy [Wabuyele et al. (2003) Journal of the American Chemical Society, 125, 6937-6945], Two-color fluorescence cross-correlation spectroscopy and usage of confocal fluorescent microscope and measurements of photon burst size, burst duration and fluorescent lifetime. These techniques usually offer higher sensitivity and faster results than the first approach.

Wabuyele et al. [Ibid], for example, employ single pair fluorescence resonance energy transfer to detect point mutations in unamplified genomic DNA. Normal DNAs are discriminated from mutant (minority) DNAs in heterogeneous populations using allele-specific primers carrying complementary stem structures with end-labels. The primers flank the point mutation in the target gene and are ligated using a thermostable ligase enzyme only when the genomic DNA carries the mutation.

Castro et al. [(1997) Analytical Chemistry, 69, 3915-3920] use two nucleic-acid probes complementary to different sites on a target DNA sequence for detecting specific nucleic acid sequences therein. The two probes are labeled with different fluorescent dyes. When mixed with a sample containing the target DNA, the probes hybridize to their respective binding sites on the same target DNA molecule and their signals therefore appear simultaneously. Coincident optical detection of both dyes at sufficient sensitivity provides the necessary specificity to detect an unamplified target DNA molecule in a homogeneous assay.

A third previously known approach to detection of specific DNA sequences uses nano-particles to translate the biorecognition event into an analytically useful signal. The detection system is either electrical (e.g., measuring the electrical resistance, a MEMS based amperometric detector as described in, for example Gau et al. ((2001) Biosensors and Bioelectronics, 16, 745-755) or optical (e.g., based on colorimetric scatter of gold nanoparticle probes as described in, for example Storhoff et al. (2004) Nature Biotechnology, 22, 883-887). These methods also offer DNA detection at low concentrations (33 fM). However, the time associated with these techniques is between 40 min to several hours.

The following table summarizes the major techniques in the 3 different approaches.

| The Method | DNA Concentration [fM] | Reaction time | Remark |
|---|---|---|---|
| Open Circle Probes + Rolling Circle Amplification to enable direct fluorescence detection | 500000 | ~1 Hour | Point mutation |
| Serial Invasive Signal Amplification Reaction and direct fluorescence detection | 1000 copies | ~4 Hours | Point mutation |
| Ligase Detection Reaction + Single Pair FRET using Fluorescence Correlation Spectroscopy | 2.5 | ~10 minutes | Point mutation |
| Two-color fluorescence cross correlation spectroscopy | 15 | >2.5 Hours | Point mutation |
| Two-color Single-Molecule photon burst detection of two differently labeled probes | 50 | >16 Hours | Specific Sequence detection |
| Single-Molecule photon burst detection using confocal fluorescent microscope | 1000 | >20 Hours | Specific Sequence detection |
| Silver-Enhanced gold nanoparticle probes and conductivity measurements | 500 | >6 Hours | Point mutation |
| MEMS based Amperometric detection using DNA hybridization and enzyme amplification | 1000 copies | 40 minutes | Specific Sequence detection |
| Gold nanoparticle probes and detection using spectrophotometer | 33 | ~2 Hours | Specific Sequence detection |

-continued

| The Method | DNA Concentration [fM] | Reaction time | Remark |
|---|---|---|---|
| Gold nanoparticle probes and detection using spectrophotometer | 50 | ~1 Hour | Point mutation |

Some previously available approaches attempt to offset limitations of a specific probe (e.g. specific activity or fluorescence intensity) by amplifying the target geometrically. Detection of a specific nucleic acid sequence often relies upon amplification of a DNA sequence via the Polymerase Chain Reaction (PCR) for geometric amplification. In some cases, a reverse transcription step is used to transform RNA to DNA which is then subject to PCR (RT-PCR). PCR can be subject to limitations including, but not limited to, nonlinearities in amplicon number with cycle number, long optimization and set up times, long run and analysis times and a high level of inaccuracy and variation (e.g. due to cross-contamination).

Sensitivity of sensing systems is often limited by background noise.

SUMMARY OF THE INVENTION

In an exemplary embodiment of the invention, there is provided a method of detecting a target within a population of molecules. The method includes:

contacting a plurality of labeled probe molecules with the population of molecules potentially containing a target of the probe molecules;

acquiring a probe specific signal emitted by the labeled probe molecules that bound to the target together with a background signal;

preferentially modulating the probe specific signal by at least one of modulating the acquisition and modulating an emission of the probe specific signal; and detecting the probe specific signal over the background signal using the preferential modulation.

Optionally, the preferentially modulating includes moving the probe molecules bound to the target in and out of an excitation beam.

Optionally, the preferentially modulating includes temporal modulation.

Optionally, the preferentially modulating includes spatial modulation.

Optionally, the preferentially modulating includes modulation of a pH of a solution containing the labeled probe molecules.

Optionally, the preferentially modulating includes a single modulation cycle.

Optionally, the preferentially modulating includes multiple modulation cycles.

Optionally, the preferentially modulating includes modifying a response of the probe molecules bound to the target to an applied excitation energy.

Optionally, the probe molecules include a molecule type selected from the group consisting of a polynucleotide, a polypeptide, a carbohydrate and an ion chelator.

Optionally, the polypeptide includes an antibody.

Optionally, the polynucleotide is selected from the group consisting of DNA, RNA and synthetic oligonucleotide.

Optionally, the target within the population of molecules includes a molecule type selected from the group consisting of a nucleic acid sequence, an amino acid sequence, a carbohydrate sequence and a feature of a protein determined by non-primary structure.

Optionally, the preferentially modulating includes establishing periodic motion of the probe molecules bound to the target.

Optionally, the establishing periodic motion includes applying an alternating field selected from the group consisting of a magnetic field and an electric field to the probe.

Optionally, the probe molecules are attached to a magnetic particle.

Optionally, the probe specific signal is a fluorescent signal.

Optionally, the probe molecules include at least one fluorescence-modifying moiety.

Optionally, the probe specific signal employs an energy transfer mechanism selected from the group consisting of fluorescent energy transfer (FET) and fluorescence resonance energy transfer (FRET).

Optionally, the detecting the probe specific signal over the background signal is accomplished within one minute of the contacting a labeled probe with the population of molecules.

Optionally, the detecting the probe specific signal over the background signal is reliably accomplished when no more than 100 copies of the target are present.

Optionally, the detecting the probe specific signal over the background signal is reliably accomplished when a concentration of the target does not exceed 1 femtomolar (fM).

Optionally, the detecting includes at least one detection type selected from the group consisting of binary detection, amplitude detection and synchronous detection.

Optionally, the background signal includes Raman scattering.

Optionally, the preferential modulation produces a probe specific signal which is ten times greater in amplitude than the background signal if the target is present.

Optionally, the preferential modulation includes increasing a local concentration of the labeled probe molecules that are bound to the target during the acquisition.

In an exemplary embodiment of the invention, there is provided a system for detecting a target within a population of molecules. The system includes:

a vessel adapted to contain a plurality of labeled probe molecules in contact with a population of molecules potentially containing a target of the probe molecules;

a fluorescent excitation source adapted to direct an excitation beam through the vessel, the beam configured to cause at least some of the probe molecules that bound to the target to emit a probe specific signal;

a detector adapted to detect the probe specific signal and produce a detection output;

a signal modulator configured to preferentially modulate at least one of the probe specific signal and the detector; and an analysis module adapted to analyze the detection output in consideration of the preferential modulation.

Optionally, the analysis module is configured to determine the presence or absence of the target within the population of molecules.

Optionally, the system includes a modulation indication source adapted to provide a modulation indication to the signal modulator and to the detector.

Optionally, the signal modulator is adapted to:
monitor an output of the signal modulator; and
provide a modulation indication to the detector responsive to the output of the signal modulator.

Optionally, the signal modulator includes an alternating field generator selected from the group consisting of an electric field generator and a magnetic field generator, the alternating field generator configured to apply power at a level suitable for frequency modulation and sufficient for moving probe molecules out of the excitation beam.

According to one aspect of the present invention there is provided a method of detecting or determining nucleic acid sequence of a bio-molecule, comprising: hybridizing a labeled probe to the bio-molecule so as to produce a hybridization indicative detectable signal; establishing a periodic motion to the labeled probe;

detecting the detectable signal synchronously with the periodic motion thereby detecting or determining the nucleic acid sequence of the bio-molecule.

According to further features in preferred embodiments of the invention described below, the establishing the periodic motion comprises applying an alternating electric field to the labeled probe.

According to still further features in the described preferred embodiments the labeled probe is attached to a magnetic particle.

According to still further features in the described preferred embodiments the establishing the periodic motion comprises applying an alternating magnetic field gradient to the labeled probe.

According to another aspect of the present invention there is provided a system for detecting or determining nucleic acid sequence of a bio-molecule being hybridized to a labeled probe capable of producing a hybridization indicative detectable signal, the system comprising: a mechanism for establishing a periodic motion to the labeled probe, the mechanism being associated with a transmission unit for transmission data characterizing the periodic motion; a detector for detecting the detectable signal and producing detection signals; and a synchronizer, for synchronizing the detection signals with the periodic motion data, so as to increase signal-to-noise ratio of the detection signals, thereby to detect or determine the nucleic acid sequence of the bio-molecule.

According to further features in preferred embodiments of the invention described below, the mechanism comprises an alternating electric field generator.

According to still further features in the described preferred embodiments the mechanism comprises an alternating magnetic field generator.

According to still further features in the described preferred embodiments the detector comprises a photomultiplier tube.

According to still further features in the described preferred embodiments the detector comprises a radioactive radiation detector.

According to still further features in the described preferred embodiments the system further comprising an excitation unit, configured for exciting the hybridization indicative detectable signal.

According to still further features in the described preferred embodiments the labeled probe comprises a fluorescent label having at least a fluorescence moiety and a fluorescence-modifying moiety, whereby hybridization of the labeled probe to the bio-molecule detectably alters fluorescence emitted by the fluorescent label.

According to still further features in the described preferred embodiments the fluorescence-modifying moiety comprises a quencher molecule.

According to still further features in the described preferred embodiments the labeled probe comprises a radioactive label.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

For purposes of this specification and the accompanying claims, the terms "label" and "labeled" and their derivatives refer to chemical moieties which are provided to contribute to generation of a signal for measurement. The terms include all signal generating moieties known in the art. It is expected that during the life of this patent, new signal generating moieties will be discovered or characterized and which can be affected by external modulation and these new signal generating moieties are incorporated a priori in the terms label and/or labeled.

For purposes of this specification and the accompanying claims, the phrase "probe molecules" indicates any identifiable substance that is used to detect, isolate, or identify another substance (i.e. a target). Probe molecules can be characterized in terms of target specificity. Target specificity is typically in the range of $10^{-3}$M to $10^{-15}$M. "Probe molecules" include, but are not limited to, an aptamer, a labeled strand of DNA that hybridizes with its complementary RNA or a monoclonal antibody that combines with a specific protein.

For purposes of this specification and the accompanying claims, the phrase "probe specific signal" refers to a signal originating from one or more labels attached to one or more probe molecules that bound to their target(s).

For purposes of this specification and the accompanying claims, the phrase "background signal" encompasses any signal that is not a probe specific signal.

For purposes of this specification and the accompanying claims, "modulating" and "modulation" indicate varying including but not limited to varying the frequency and/or amplitude and/or phase.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Exemplary embodiments of the invention comprise a method and system for detecting presence or absence of a target within a population of biomolecules. Optionally, the target is indicative of a specific sequence, such as a nucleotide sequence or an amino acid peptide sequence. Exemplary embodiments of the invention employ a probe labeled so as to produce a binding (e.g. hybridization) indicative detectable signal. The labeled probe can be contacted with a population of molecules to analyzer presence and/or amount of a target. Optionally, the label comprises a fluorescent dye and a dark quencher so that when the probe contacts the target sequence, the fluorescent dye molecule is disconnected from the dark quencher and fluorescent light is produced.

Some exemplary embodiments of the invention relate to a method of determining presence or absence of a target within a population of molecules. In general, methods according to exemplary embodiments of the invention employ preferential modulation of probe that has bound to one or more targets to improve a signal to noise ratio.

According to some embodiments of the invention, improvement in signal to noise ratio synchronization of signal detection and modulation brings a larger number of labeled probe molecules into an excitation beam at one time. The larger number of labeled probe molecules contribute to an increase in probe specific signal. Background signal remains unaffected.

Figure 8:
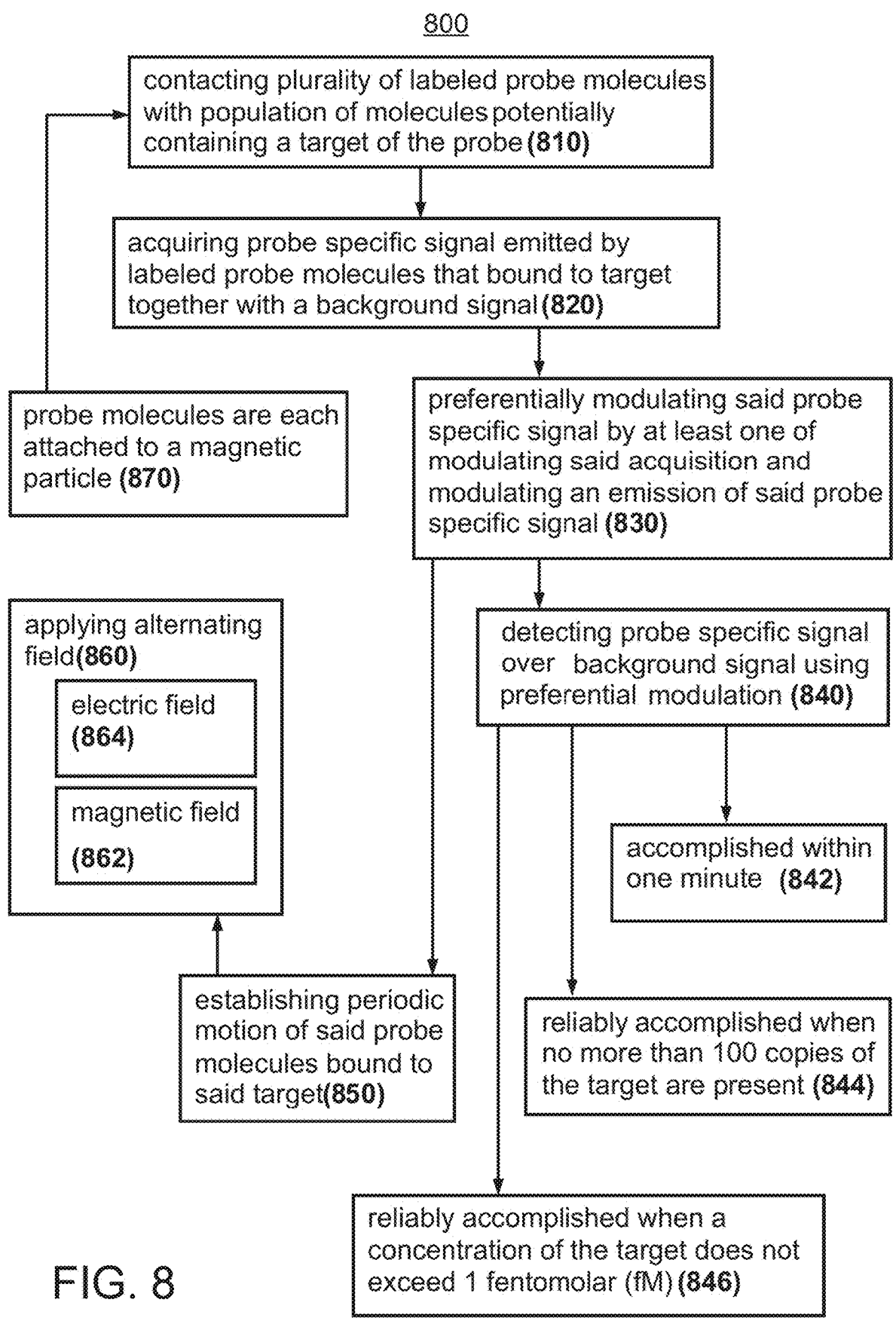
FIG. 8 is a simplified flow diagram of a method according to an exemplary embodiment of the invention.

FIG. 8 is a simplified flow diagram of an exemplary method 800. According to exemplary method 800, a plurality of labeled probe molecules are contacted 810 with a population of molecules potentially containing a target of the probe molecules.

Optionally, conditions for contacting 810 are adjusted to favor specific target/probe binding and/or to discourage nonspecific binding of the probe to non-target substrates as is known in the art.

Adjustment of conditions for contacting 810 optionally includes adjustment of temperature and/or adjustment of osmolarity and/or adjustment of detergent concentration and/or adjustment of probe amount and/or adjustment of target amount. In an exemplary embodiment of the invention, specificity of interaction between target and labeled probe can be confirmed by attempting to dampen a signal using unlabeled probe at a high concentration to saturate available target molecules. While exemplary embodiments described herein relate to target and probe in solution, principles described herein are also applicable to techniques where the target is immobilized on a solid substrate (e.g. a nitrocellulose or nylon membrane or beads (e.g. agarose or sepharose or a gel)).

According to depicted exemplary method 800, a probe specific signal is then acquired 820 from labeled probe molecules that bound to the target together with a background signal. In exemplary embodiments of the invention employing laser florescence the background signal comprises Raman scattering.

In an exemplary embodiment of the invention, once a specific probe molecule has bound to a target molecule, it becomes capable of emitting the probe specific signal. In some cases, emission of the probe specific signal continues even if the binding does not continue. In some exemplary embodiments of the invention, preferentially modulating includes modifying a response of probe molecules bound to the target to an applied excitation energy.

According to depicted exemplary method 800 preferential modulation 830 of the probe specific signal is effected. Preferential modulation may mean that a background signal is modulated less or is not modulated. Optionally, the preferential modulation includes modulating acquisition 820 and/or modulating an emission of the probe specific signal.

In an exemplary embodiment of the invention, detecting 840 of the probe specific signal over the background signal uses the preferential modulation. Optionally, the preferential modulation contributes to an increase in sensitivity and/or specificity.

Optionally, the preferential modulation comprises moving the probe molecules bound to the target in and out of an excitation beam. According to various exemplary embodiments of the invention the preferential modulation comprises temporal modulation and/or spatial modulation. Optionally, the preferential modulation comprises a single modulation cycle or multiple modulation cycles. Optionally, 10, 25, 50, 100, 200, 200, 800 or 1200 or intermediate or greater numbers of modulation cycles are employed. Optionally, increasing a number of modulation cycles contributes to an increase in sensitivity or reliability of detection. Optionally, increasing a number of modulation cycles at a given modulation frequency contributes to an increase in detection time. In some exemplary embodiments of the invention, a signal change after modulation ceases is informative.

According to various exemplary embodiments of the invention, the probe molecules include molecule types such as nucleic acid (e.g. DNA or RNA), and/or a peptide and/or a protein (e.g. an antibody or a lectin) and/or an ion chelator. Optionally, labeled probes can be provided as DNA or RNA and may be provided as oligomers and/or as restriction fragments and/or as amplified PCR products. Restriction fragments can be prepared from, for example, genomic DNA, cDNA, plasmids, cosmids, phagemids or phages.

According to various exemplary embodiments of the invention, the target within the population of molecules comprises one or more molecule types selected from the group consisting of a nucleic acid sequence, an amino acid sequence, a carbohydrate or carbohydrate sequence, an ion and a feature of a protein determined by non-primary structure (e.g. a post-translational modification, such as tyrosine phosphorylation).

Optionally, method 800 employs a DNA target and a DNA probe, an RNA probe and a DNA target, a DNA target and a protein probe (e.g. a helix turn helix, a zinc finger, a leucine zipper, a winged helix, an ETS domain, a helix loop helix, an immunoglobulin fold, a homeodomain and a B3 DNA binding domain), a protein probe and a carbohydrate target (e.g. lectin/carbohydrate pair), a chelator probe and an ion target (e.g. EDTA/Calcium) and or a protein probe and a protein target (e.g. antibody/epitope pair).

U.S. Pat. No. 7,090,995 describes signal generating moieties which generate a signal proportional to an amount of bound ion.

In an exemplary embodiment of the invention, preferentially modulating 830 includes establishing periodic motion 850 of the probe molecules bound to the target. Optionally, establishing periodic motion 850 includes applying an alternating field 860 such as a magnetic field 862 and/or and an electric field 864 to cause a signal which varies in intensity according to a frequency of the applied field.

In some exemplary embodiments of the invention, probe molecules are each attached 870 to a magnetic particle. Optionally, attachment 870 of probe molecules to magnetic particles makes the probe molecules more sensitive to application 860 of an alternating field. In an exemplary embodiment of the invention, probe molecules carrying a magnetic bead which have not bound to target move in the alternating field according to changes in field polarity but do not contribute to the probe specific signal.

In other exemplary embodiments targets and/or probes and/or molecules are sufficiently sensitive to the alternating field (e.g. due to an inherent molecular charge) that they can be moved by the alternating field without a bead.

According to many exemplary embodiments of the invention, the probe specific signal is a fluorescent signal. Optionally, the probe molecules include at least one fluorescence-modifying moiety. In exemplary embodiments of the invention, the probe specific signal employs an energy transfer mechanism. Exemplary energy transfer mechanisms include, but are not limited to, fluorescent energy transfer (FET) and fluorescence resonance energy transfer (FRET).

In an exemplary embodiment of the invention, detecting 840 the probe specific signal over said background signal is accomplished within one minute 842 of the contacting of labeled probe with the population of molecules.

In an exemplary embodiment of the invention, detecting 840 the probe specific signal over said background signal is reliably accomplished when no more than 100 copies of the target are present 844.

In an exemplary embodiment of the invention, detecting 840 the probe specific signal over said background signal is reliably accomplished when a concentration of the target does not exceed 1 femtomolar (fM) 846.

In an exemplary embodiment of the invention, use of preferential modulation 830 contributes to increased detection sensitivity and/or detection speed.

According to various exemplary embodiments of the invention, detecting 840 includes binary detection and/or amplitude detection and/or synchronous detection. Binary detection provides a qualitative output (target is or is not present). Amplitude detection provides a quantitative or semi-quantitative indication of target amount. Synchronous detection is a method of detection employs a known pattern (e.g. periodic) of the signal to help decide if there is and/or what the signal is.

In an experiment exemplifying application of the invention, preferential modulation 830 produced a probe specific signal 26 times greater than the background at concentration of $3 \cdot 10^{-12}$M. thereby indicating a detection sensitivity of $1.1 \cdot 10^{-13}$M. In other exemplary embodiments of the invention a factor of 1.001 is employed. In the experiment, 7.2 nanomole of a 17 bp DNA probe was labeled with 6-Carboxyfluorescein (6-Fam) and biotin on the same nucleotide at the 5' end (5' (C6-FAM)/biotin-dTCT). The probe was sequentially diluted in ddH$_2$O. Streptavidin-coupled magnetic beads with 2.8 µm diameter were used to bind the oligonucleotides. Each bead binds to ~1938 oligonucleotides. In order to demonstrate capability of the detection system, two solutions were generated.

A "reference solution" contained 75 µl of magnetic beads in buffer Tris-HCl at $1.54 \cdot 10^{-15}$M without any fluorescent dye.

A second solution was prepared by first mixing 50 µl of $5.56 \cdot 10^{-14}$M magnetic beads with $5 \cdot 10^{-9}$M of fluorescent labeled DNA probe. After 30 min beads connected to the fluorescent labeled DNA were washed and resuspended in 100 µl of a 50:50 mixture of ddH$_2$O and Tris-HCl buffer. The solution was further diluted to its 1:18 part to produce the "test solution" containing $1.54 \cdot 10^{-15}$M of magnetic beads and $3 \cdot 10^{-12}$M of fluorescent labeled probes. The reference and test solutions were tested in the detection system.

For this exemplary experiment, laser output power was ~3.2 mW and the current modulation was performed at ~6 Hz. It appears that reflections of the laser beam from the aggregated beads moving in and out the laser spot were also detected and demodulated by the lock-in amplifier. However, while the produced signal of the "reference solution" (without fluorescent molecules) was ~2 mV, the produced signal of the "test solution" (with the fluorescent molecules) was ~52 mV, which yields a signal to noise ratio of ~26. These preliminary results represent a sensitivity of ~$1.1 \cdot 10^{-13}$M of fluorescent labeled DNA probes. It should be noted that the signal was produced almost immediately (i.e. visually discernible within several seconds).

This exemplary experiment demonstrates both increased sensitivity and increased rapidity with respect to previously available alternatives.

In an exemplary embodiment of the invention, preferential modulation 830 increases a local concentration of labeled probe molecules that are bound to the target during acquisition 820. Optionally, increasing the local concentration of labeled probe molecules locally amplifies the probe specific signal per unit area and/or improves a signal to noise ratio. In an exemplary embodiment of the invention, detecting 840 is performed where local concentration of is increased.

Figure 9:
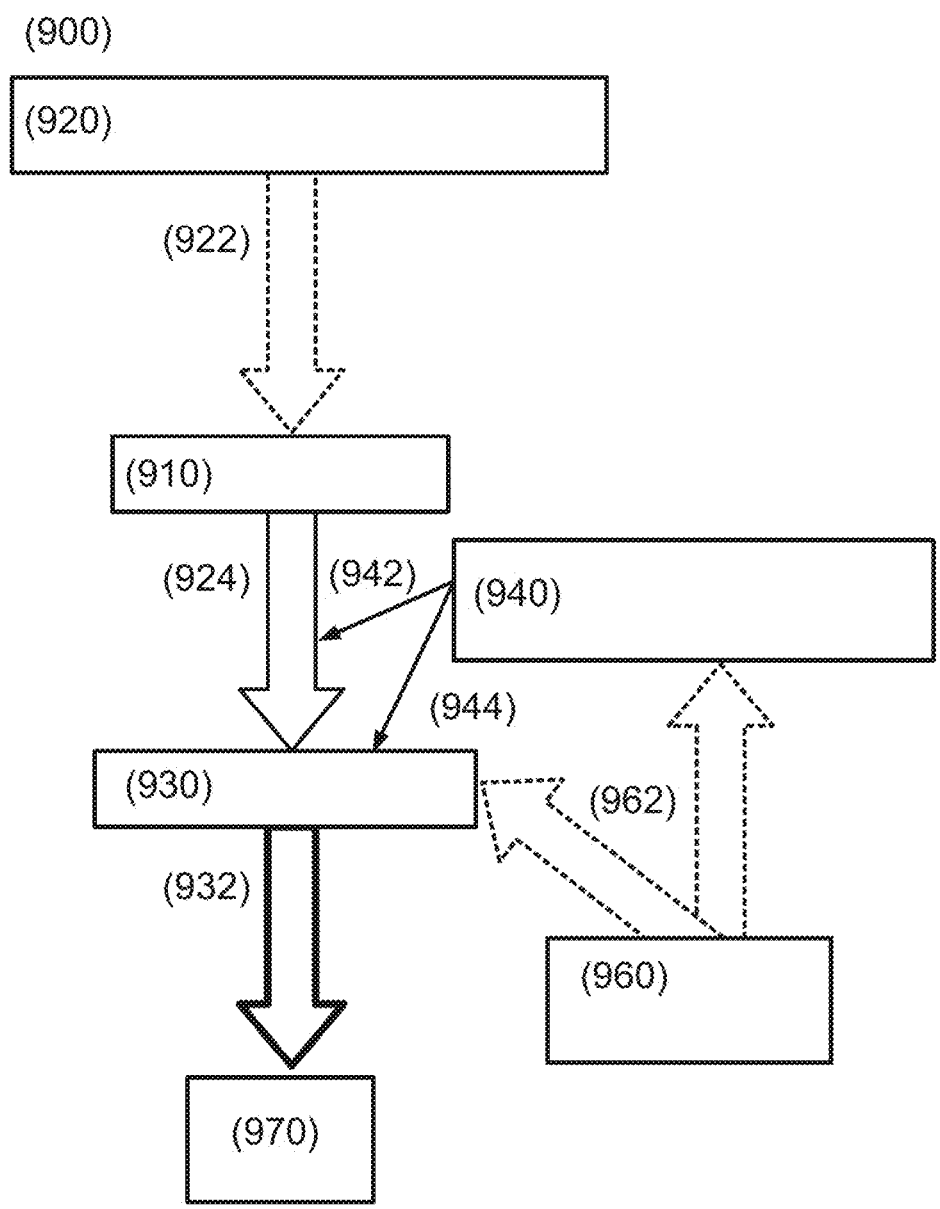
FIG. 9 is a schematic representation of an exemplary amplification and detection system according to an embodiment of the invention.

FIG. 9 is a schematic representation of an exemplary detection system 900. In an exemplary embodiment of the invention, system 900 is used to determine presence or absence of a target, optionally a sequence, within a population of molecules. The molecules and the target are as described elsewhere in this application.

Depicted exemplary system 900 includes a vessel 910 adapted to contain a plurality of labeled probe molecules in contact with a population of molecules potentially containing a target of the probe molecules. Optionally, the contact between the probe molecules and the population of molecules is established in vessel 910 or prior to introduction in vessel 910.

Depicted exemplary system 900 also includes a fluorescence excitation source 920 adapted to direct an excitation beam 922 through vessel 910. In an exemplary embodiment of the invention, beam 922 is configured to cause at least some of the probe molecules bound to the target to emit a probe specific signal 924 for acquisition 820.

Depicted system 900 also includes a detector 930 adapted to detect probe specific signal 924 and produce a detection output 932. In an exemplary embodiment of the invention, detector 930 comprises a PMT.

Optionally, a signal modulator 940 is configured to preferentially modulate probe specific signal 924 and detector 930.

In an exemplary embodiment of the invention, an analysis module 970 analyzes detection output 932 in consideration of preferential modulation. As described hereinabove analysis module 970 can employ, for example, Binary detection, Amplitude or Synchronous detection. Optionally, analysis module 970 determines presence or absence of the target within the population of molecules.

In some exemplary embodiments of the invention, system 900 includes a modulation indication source 960 which provides a modulation indication 962 to signal modulator 940 and to detector 930. In an exemplary embodiment of the invention, modulation indication 962 synchronizes operation of signal modulator 940 and detector 930.

In other exemplary embodiments of the invention, signal modulator 940 monitors its own output 942 and provides a modulation indication 944 to detector 930 responsive to output 942.

Optionally, output 942 and/or or modulation indication 962 comprise modulation frequency information and/or modulation phase information.

According to some exemplary embodiments of the invention, signal modulator 940 comprises an alternating field generator (e.g. electric field generator or magnetic field generator). In an exemplary embodiment of the invention, the alternating field generator applies power at a level suitable for frequency modulation and/or sufficient for moving probe molecules out of the excitation beam.

Optionally, analysis module 970 considers whether detection output 932 meets or exceeds a predetermined threshold. In some exemplary embodiments of the invention, the threshold is defined in terms of an amplitude fluctuation during periodic motion produced by signal modulator 940 and/or in terms of rate of increase of detection output 932 as additional bound probe molecules are recruited.

Optionally, analysis module 970 and/or a user of system 900 can change modulation parameters if detection output 932 does not meet the predetermined threshold. The user and/or analysis module 970 optionally initiate a scan of modulation frequency in order to increase detection output 932. A frequency contributing to an increase in output 932 optionally varies with one or more of applied power, distance to travel and probe mechanical behavior.

Exemplary embodiments of the invention are suitable for determining presence or absence, and optionally amount, of specific sequence(s) (e.g. nucleic acid and/or peptide and/or carbohydrate) within a population of molecules. Described methods and systems of the exemplary embodiments of the invention efficiently amplify fluorescence from a labeled probe from background fluorescence. This amplification contributes to an ability to reliably detect a weak fluorescent signal without target amplification. According to exemplary embodiments of the invention, amplification and detection are performed without separating the target from non-target portions of the molecules.

Exemplary systems and methods described herein allow implementation of a wide range of biological applications which require detection and/or identification of specific target sequences, especially at low concentrations (e.g. $10^{-12}$, $10^{-13}$, $10^{-14}$ or $10^{-15}$ Molar or lower or intermediate concentrations). For example, systems and methods as described herein can be used for non-invasive method of fetal genotyping (e.g., determination of Rhesus D status, fetal sex, cystic fibrosis and sickle cell anemia) by analysis of fetal DNA presented in the plasma of pregnant women and/or for determining chick gender in ovo and/or for analysis of molecular markers associated with various diseases (e.g. different types of cancer, HIV, rabies, hoof and mouth disease and prion mediated diseases) in non-fetal tissue and/or for pathogen (e.g., *E. coli.*, *C. botulinum* and *B. anthracis*) detection in environmental samples or food samples.

In an exemplary embodiment of the invention, non-invasive fetal genotyping as described hereinabove can replace or augment assays which rely upon sampling of embryonic fluid.

According to various exemplary embodiments of the invention, target size varies. Optionally, a target can be as small as a single nucleotide mutation or as large as a chromosomal region. Optionally, a probe specific to a small target is used as indicative of changes in a chromosomal region.

In an exemplary embodiment of the invention, early detection of disease associated markers using exemplary embodiments of the invention can contribute to increased therapy efficacy and/or increased average survival time.

According to previously available alternatives, chick gender is determined post hatching, most often manually by a feathering technique. Exemplary embodiments of the invention can be employed to determine chick gender in ovo. Early gender determination in ovo can reduce costs in the poultry industry, for example by allowing elimination of a non-desired gender from an incubation cycle at an early stage. It is envisioned that operational costs of incubation could be reduced by as much as 30 to 50% in this way. This approach has utility in the egg industry, as well as in breeding programs where separate male and female lines are produced for subsequent cross breeding.

From the humanitarian standpoint, in ovo gender determination of poultry can prevent massive killing of new born male chicks in the layer industry. The system and method of the present embodiments can also be used in many other applications, including, without limitation, rapid detection of pathogenic (e.g., *Bacillus anthracis*) in environmental samples, and the like.

According to many exemplary embodiments of the invention, signal modulator 940 causes modulation of probe specific signal 924 and/or detector 930 with a frequency of 1-10 Hz.

Optionally, a higher frequency can be employed (e.g. 100. 1000 or 10,000 Hz or intermediate or higher frequencies). Optionally, a higher frequency can compensate for instability of excitation beam 922. In an exemplary embodiment of the invention, multiple modulations within a stable time contribute to the compensation. In an exemplary embodiment of the invention, a frequency is selected so that a combination of frequency and power has no significant biological and/or chemical effect.

Optionally, a lower freq, (e.g. 0.1 Hz) is employed. In an exemplary embodiment of the invention, a lower frequency can be employed despite instability of excitation beam 922. Optionally, monitoring of instability of excitation beam 922 can be used as an input for additional signal processing, for example, for amplitude correction In an exemplary embodiment of the invention, method 800 and/or system 900 do not move water. Optionally, method 800 and/or system 900 can be modified to move water, if advantageous. It may be advantageous to move water if for example, spinning, concentrates the probe.

In an exemplary embodiment of the invention, modulation can cause change of light polarization. Optionally, polarization can be detected using an analyzing polarizer. In an exemplary embodiment of the invention, a probe with polarizable modulation is employed.

In some exemplary embodiments of the invention modulation is achieved by spatial arrangement. For example, a standing acoustic wave or centrifugation can arrange beads or targets in a pattern. This pattern can be detected by moving the laser beam or by its expected Bragg diffraction/scattering, which is at a specific angle. Alternatively, or additionally, the acoustic wave can be used to move the beads.

While exemplary embodiments of the invention are explained herein in detail, it is to be understood that the invention is not limited in its application to the details of construction and the arrangement of the components set forth in this specification description or illustrated in the drawings. The invention is capable of other embodiments or of being practiced or carried out in various ways. Also, it is to be understood that the phraseology and terminology employed herein is for the purpose of description and should not be regarded as limiting.

As used herein, "nucleic acid" refers to DNA, RNA, single-stranded or double-stranded and any chemical modifications thereof. Modifications include, but are not limited to, those which provide other chemical groups that incorporate additional charge, polarizability, hydrogen bonding, electrostatic interaction, and functionality to the nucleic acid. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

As used herein, "fluorescent molecule" or "fluorescent moiety" refers to a molecule or molecules that, when excited with light having a selected wavelength, emits light of a different wavelength. Fluorescent molecules or moieties may also be referred to as "fluorophores".

As used herein, "fluorescence-modifying molecule" or "fluorescence-modifying moiety" refers to a molecule or molecules that can alter in any way the fluorescence emission from a fluorescent molecule or moiety. A fluorescence-modifying molecule or moiety generally accomplishes this through an energy transfer mechanism. Depending on the identity of the fluorescence-modifying molecule or moiety, the fluorescence emission can undergo a number of alterations, including, but not limited to, attenuation, complete quenching, enhancement, a shift in wavelength, a shift in polarity, a change in fluorescent lifetime. One example of a fluorescence-modifying molecule or moiety is a quenching molecule or moiety.

As used herein, "quenching molecule" or "quenching moiety" refers to any fluorescence-modifying molecule or moiety that can attenuate at least partly the light emitted by a fluorescent molecule or moiety. This attenuation is referred to herein as "quenching". Hence, illumination of the fluorescent molecule or moiety in the presence of the quenching molecule or moiety leads to an emission signal that is less intense than expected, or even completely absent. Quenching occurs through energy transfer between the fluorescent molecule or moiety and the quenching molecule or moiety As used herein, "energy transfer" refers to the process by which the fluorescence emission of a fluorescent molecule or moiety is altered by a fluorescence-modifying molecule or moiety. Fluorescence emission from the fluorescent molecule or moiety is attenuated (quenched) if the fluorescence-modifying molecule or moiety is a quenching molecule or moiety. Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. Energy transfer is also referred to herein as fluorescent energy transfer or FET.

As used herein, "energy transfer pair" refers to any two molecules that participate in energy transfer. Typically, one of the molecules acts as a fluorescent molecule, and the other acts as a fluorescence-modifying molecule. The preferred energy transfer pair of the instant invention comprises a fluorescent molecule and a quenching molecule. In some cases, the distinction between the fluorescent molecule and the fluorescence-modifying molecule may be blurred. For example, under certain circumstances, two adjacent fluorescein molecules can quench one another's fluorescence emission via direct energy transfer. For this reason, there is no limitation on the identity of the individual members of the energy transfer pair in this application. All that is required is that the spectroscopic properties of the energy transfer pair as a whole change in some measurable way if the distance between the individual members is altered by some critical amount.

"Energy transfer pair" is used to refer to a molecule of molecules that form a single complex within which energy transfer occurs. Such complexes may comprise, for example, two fluorescent molecules which may be different from one another and one quenching molecule, two quenching molecules and one fluorescent molecule, or multiple fluorescent molecules and multiple quenching molecules. In cases where there are multiple fluorescent molecules and/or multiple quenching molecules, the individual molecules may be different from one another.

As used herein, "fluorescence resonance energy transfer" or "FRET" refers to an energy transfer phenomenon in which the light emitted by the excited fluorescent molecule is absorbed at least partially by a fluorescence-modifying molecule. If the fluorescence-modifying molecule is a quenching molecule, then that molecule can either radiate the absorbed light as light of a different wavelength, or it can dissipate it as heat. FRET depends on an overlap between the emission spectrum of the fluorescent molecule and the absorption spectrum of the quenching molecule. FRET also depends on the distance between the quenching molecule and the fluorescent molecule. Above a certain critical distance, the quenching molecule is unable to absorb the light emitted by the fluorescent molecule, or can do so only poorly.

As used herein "direct energy transfer" refers to an energy transfer mechanism in which passage of a photon between the fluorescent molecule and the fluorescence-modifying molecule does not occur. Without being bound by a single mechanism, it is believed that in direct energy transfer, the fluorescent molecule and the fluorescence-modifying molecule interfere with each others electronic structure. If the fluorescence-modifying molecule is a quenching molecule, this will result in the quenching molecule preventing the fluorescent molecule from even emitting light.

In general, quenching by direct energy transfer is more efficient than quenching by FRET. Indeed, some quenching molecules that do not quench particular fluorescent molecules by FRET (because they do not have the necessary spectral overlap with the fluorescent molecule) can do so efficiently by direct energy transfer. Furthermore, some fluorescent molecules can act as quenching molecules themselves if they are close enough to other fluorescent molecules to cause direct energy transfer. For example, under these conditions, two adjacent fluorescein molecules can quench one another's fluorescence effectively. For these reasons, there is no limitation on the nature of the fluorescent molecules and quenching molecules useful for the practice of this invention.

In achieving specific target (e.g. DNA sequence or epitope) a high level of noise caused by non-specific fluorescence (e.g. from scattering of light from the solution) coupled with a low level of fluorescent signal is a common problem. Nonetheless, fluorescent detection without amplification of the target offers a way to avoid problems associated with PCR and/or to detect non-nucleic acid targets. In an exemplary embodiment of the invention, fluorescence resonance energy transfer (FRET) is used to provide a signal indicative of target/probe binding at a level well above background.

Figure 1:
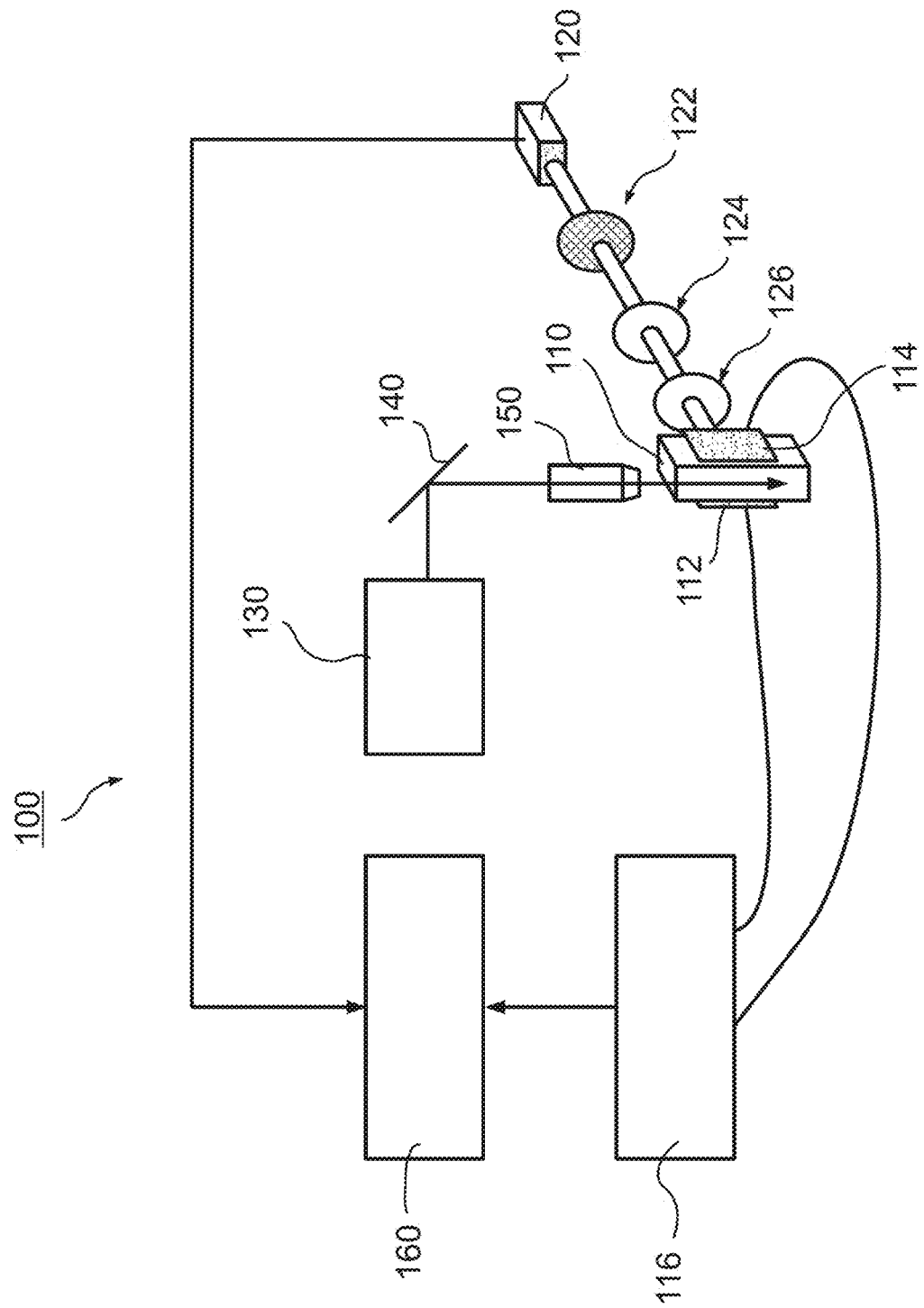
FIG. 1 is a schematic representation of an exemplary laser excitation system for use in the context of some exemplary embodiments of the invention.

In various exemplary embodiments of the invention a probe is labeled so as to produce a hybridization indicative detectable signal and contacted with a population of molecules being analyzed for presence of a target. A representative example of a labeled probe suitable for the present embodiments, includes, without limitation, TaqMan® probe labeled with a fluorescent dye and a dark quencher. The labeled probe can be used to discriminate the target sequence. When the target sequence is detected, the fluorescent dye molecule is disconnected from the dark quencher and fluorescent light is produced. FIG. 1 illustrates schematically a laser excitation system 100 for use in the context of some exemplary embodiments of the invention.

In FIG. 1, an excitation laser beam 130 is focused, optionally by means of a mirror 140, through by a microscope objective 150 into a cuvette 110 containing a sample comprising a population of molecules in solution and a labeled probe. The cuvette can be, for example a 2×2 mm square cross section quartz cell.

In an exemplary embodiment of the invention, cuvette 110 comprises two electrode poles 112 and 114 connected to a high voltage modulator 116. Optionally, modulator 116 applies an AC voltage with a defined frequency to poles 112 and 114. In an exemplary embodiment of the invention, the frequency is less than 60, optionally 40, optionally 20, optionally 10, optionally 5, optionally 3, optionally 2 optionally 1 Hz or intermediate values.

In an exemplary embodiment of the invention, a labeled probe comprises a nucleic acid probe (e.g. oligonucleotide or restriction fragment or PCR product) characterized by a negative charge. Optionally, the negative charge of the probe causes a fluorescent label attached to the probe to move orthogonally in and out of a beam from laser 130 according to the frequency of modulator 116. The orthogonal motion causes pulses of light which emanate from cuvette 110 towards a detection unit 120 (e.g. a photomultiplier (PMT)) and optionally demodulated by a Lock-In Amplifier 160. Synchronous detection dramatically decreases problems associated with background noise (e.g., Raman scattering of the solvent) and potentially increases detection sensitivity by two orders of magnitude or more.

In the depicted embodiment, light emanating from cuvette 110 passes through one or more optional elements including, but not limited to, a focusing lens 126, a spatial or spectral filter (e.g. a slit) 124 and a bandpass filter 122.

Figure 2:
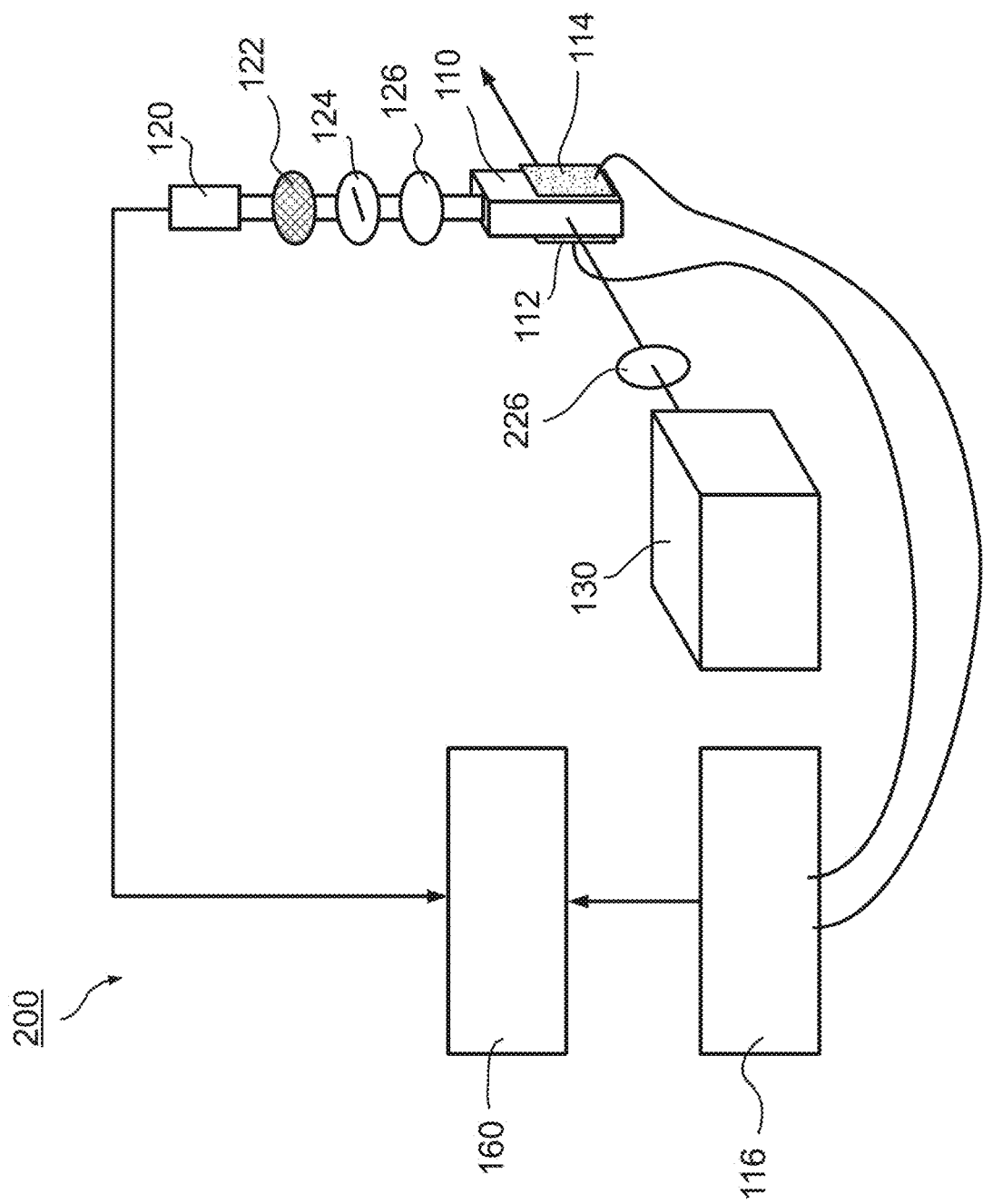
FIG. 2 is a schematic representation of an additional exemplary laser excitation system for use in the context of some exemplary embodiments of the invention.

FIG. 2 illustrates schematically another laser excitation system 200 for use in the context of other exemplary embodiments of the invention. In system 200, microscope objective 150 and optional mirror are replaced by a focusing lens 226.

Optionally, system 100 and/or 200 can be configured to perform automated and/or a manual analysis of light arriving at detector 120. Manual evaluation can be performed, for example, by visual evaluation of an image on a display screen.

Modulation of the fluorescent dye can also be done by a sinusoidal magnetic field gradient (e.g., using two coils [Katsura et al. (2001) Superconductor Science and Technology, 14, 1131-1134]). According to exemplary embodiments of the invention employing this technique, the labeled probe (e.g., TaqMan® probe) is double labeled with a fluorescent dye and Biotin on the same nucleotide at the 5' end. The dark quencher is connected at the 3' end. When the target DNA sequence is detected, the fluorescent dye molecule, still connected to the biotin, is separated from the dark quencher and fluorescent light can be produced. The biotin is attached to streptavidin-coupled magnetic beads. The external magnetic modulation sets the fluorescent molecule, which is connected via the biotin and avidin to magnetic particles, in a sinusoidal motion. The sinusoidal motion, in and out of the orthogonal laser beam, produces a sinusoidal pulse of fluorescent light which is collected by the PMT and demodulated by a Lock-In Amplifier.

Figure 3:
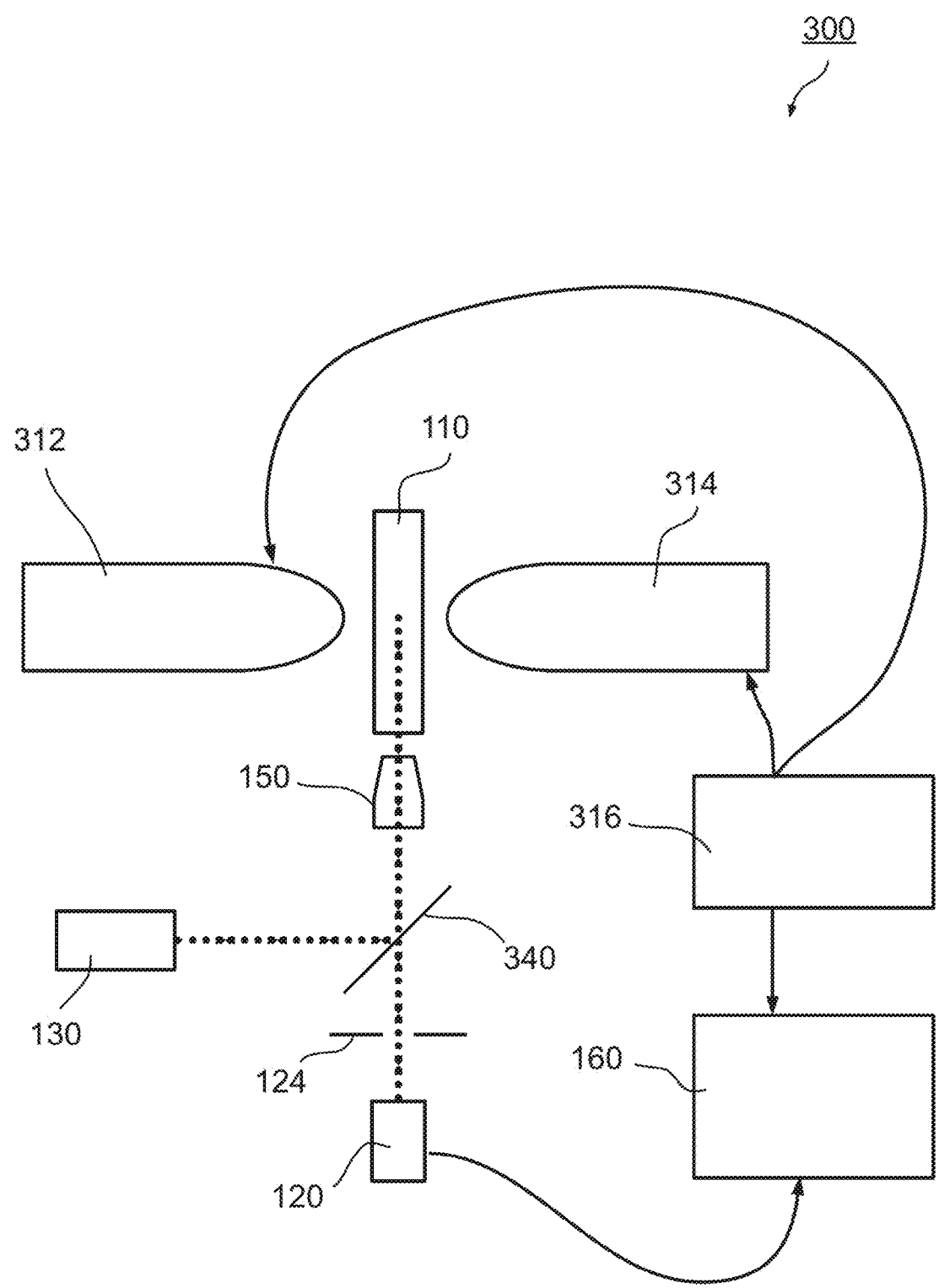
FIG. 3 is a schematic representation of a magnetic modulation system for use in the context of some exemplary embodiments of the invention.

FIG. 3 depicts an exemplary embodiment of a magnetic modulation system 300 suitable for use in the context of some embodiments of the invention. In system 300 a beam emanating from laser 130 passes through beam splitter 340 and is directed, optionally via microscope objective 150, to cuvette 110 containing the solution with biomolecules comprising target and the labeled probe. Fluorescent light created by laser excitation of the labeled probe travels back though beam splitter 340, optionally via microscope objective 150) to detector 120 (depicted as a PMT). In the depicted embodiment, electrodes 112 and 114 are replaced by electromagnetic poles 312 and 314 and voltage modulator 116 is replaced by current modulator 316. Optionally, output from PMT 120 regulates current modulator 316 via lock in amplifier 160.

In some embodiments, magnetic modulation system 300 is more efficient than system 100 and/or system 200. In an exemplary embodiment of the invention, the magnetic gradient created by electromagnetic pole (312 or 314) attracts all the magnetic particles in the solution and forms a very narrow path between the two poles. For example, in a 50 micro litter solution containing $1 \times 10^{-13}$ Molar target (connected to magnetic particles), all 3,000,000 target molecules (e.g. specific DNA sequences) are collected in a narrow line between the poles. Optionally, this collection creates a high intensity fluorescent signal which contributes to an ability to detect a low target concentration in the presence of background fluorescence.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

As noted above, direct detection of fluorescent light is limited by the background noise contributed mainly by the light scattered from the solvent (e.g. elastic Rayleigh scattering of the laser wavelength and red shifted Raman scattering). Residual fluorescence increases rapidly with the energy of the exciting photon. Thus working in the red part of the spectrum will reduce the background problem. A rough estimation for the direct detection limitation due to Raman scattering is considered in the following calculation. An excitation laser beam (Argon laser model 262A-01, $\lambda$=488 nm, output power P=1 mW, beam waist $\omega$=20 μm) is focused into a 0.5×5 mm (I.D) large ratio rectangle borosilicate tube filled with water based buffer and 6-FAM (6-Carboxyfluorescein) as the fluorescent dye. In water, the dominant Raman line is produced by the fundamental O—H stretch mode of the water molecule. The Raman frequency shift is 3400 cm$^{-1}$ (i.e. for excitation laser wavelength at 488 nm, the Raman peak is at 585 nm) and the cross section is:

$$\sigma = 4\pi \cdot 8.2 \cdot 10^{-34} \left[ \frac{m^2}{molecule} \right]$$

The detection volume is:
$V = \pi \cdot r^2 \cdot L = \pi (20 \; \mu m)^2 \cdot 5 \; mm = 6.28 \cdot 10^{-9}$ [litter]

The Laser Intensity is:

$$I = \frac{P}{A} = \frac{1 \; mW}{\pi \cdot (20 \; \mu m)^2} = 795774 \left[ \frac{W}{m^2} \right]$$

The Number of water molecule in the detection volume is:
$N = C \cdot V \cdot N_a = 55.5 \; Molar \cdot 6.28 \cdot 10^{-9} \; litter \cdot 6.02 \cdot 10^{23} = 2.1 \cdot 10^{17}$ [molecules]

The Photon absorption rate of single molecule water at 488 nm is:

$$W = \frac{\sigma \cdot I}{h \cdot \upsilon} = \frac{\sigma \cdot I \cdot \lambda}{h \cdot c} = \frac{4\pi \cdot 8.2 \cdot 10^{-34} \cdot 795774 \cdot 488 \cdot 10^{-9}}{6.62 \cdot 10^{-34} \cdot 3 \cdot 10^8} = 2.01 \cdot 10^{-8} \left[ \frac{photons}{sec} \right]$$

The Photon emission rate of all water molecules is (assuming the quantum efficiency is 1):

$$\overline{W} = W \cdot N 2.01 \cdot 10^{-8} \cdot 2.1 \cdot 10^{17} = 4.22 \cdot 10^9 \left[ \frac{photons}{sec} \right]$$

Inhomogeneous broadening of Raman linewidth results with less than 0.0001 of peak power at detection bandwidth (515-565 nm). Thus, the total Photon emission rate of all water molecules at the range 515-565 nm is:

$$\overline{W}_{Water} = \overline{W} \cdot 0.0001 = 4.22 \cdot 10^5 \left[ \frac{photons}{sec} \right]$$

Photon Emission Rate of the Fluorescent Dye
(6-FAM)

Assuming extinction coefficient $\varepsilon$=83000[1/(Molar·cm)], the absorption cross section of 6-FAM is (Beer Lambert Law):

$$\sigma = \frac{\ln(2) \cdot 1000}{\log(2) \cdot N_a} \cdot \varepsilon \left[ \frac{1}{Molar \cdot cm} \right] = 3.17 \cdot 10^{-16} [cm^2] = 3.17 \cdot 10^{-20} [m^2]$$

Hence, the photon absorption rate of a single 6-FAM molecule is:

$$W = \frac{\sigma \cdot I \cdot \lambda}{h \cdot c} = \frac{3.17 \cdot 10^{-20} \cdot 795774 \cdot 488 \cdot 10^{-9}}{6.62 \cdot 10^{-34} \cdot 3 \cdot 10^8} = 61985 \left[ \frac{photons}{sec} \right]$$

In order to achieve signal to noise ratio of $\sqrt{SNR}$=10, the fluorescent emission rate of the 6-FAM should be at least 100 times higher than water:

$$\overline{W}_{6-FAM} = \overline{W}_{Water} \cdot 100 = 4.22 \cdot 10^7 \left[ \frac{photons}{sec} \right]$$

Therefore, assuming fluorescent quantum yield of $\phi_F$=0.9, the number of the 6-FAM molecules should be:

$$N = \frac{\overline{W}}{\phi_F \cdot W} = \frac{4.22 \cdot 10^7}{0.9 \cdot 61985} \cong 756 [molecules]$$

A rough estimation of the minimal concentration for direct detection (assuming $\sqrt{SNR}$=10) is:

$$C = \frac{N}{V \cdot N_a} = \frac{756}{6.02 \cdot 10^{23} \cdot 6.28 \cdot 10^{-9}} \cong 2 \cdot 10^{-13} [Molar]$$

For example, the limitation of commercially available detection systems:
(1) Molecular Devices, SpectraMax M5: Intensity detection limit 5·10$^{-12}$ Molar.
(2) Molecular Devices, Analyst HT: Intensity detection limit 5·10$^{-12}$ Molar.

Figure 4B:
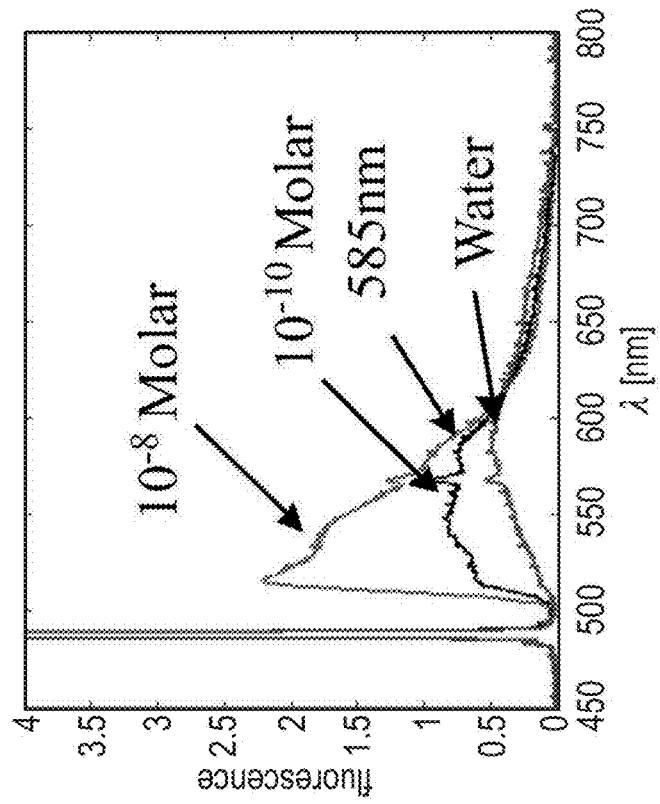
FIGS. 4a and 4b are histograms of fluorescence as a function of wavelength for a 6 FAM fluorophore detected directly according to exemplary embodiments of the invention.
Figure 4A:
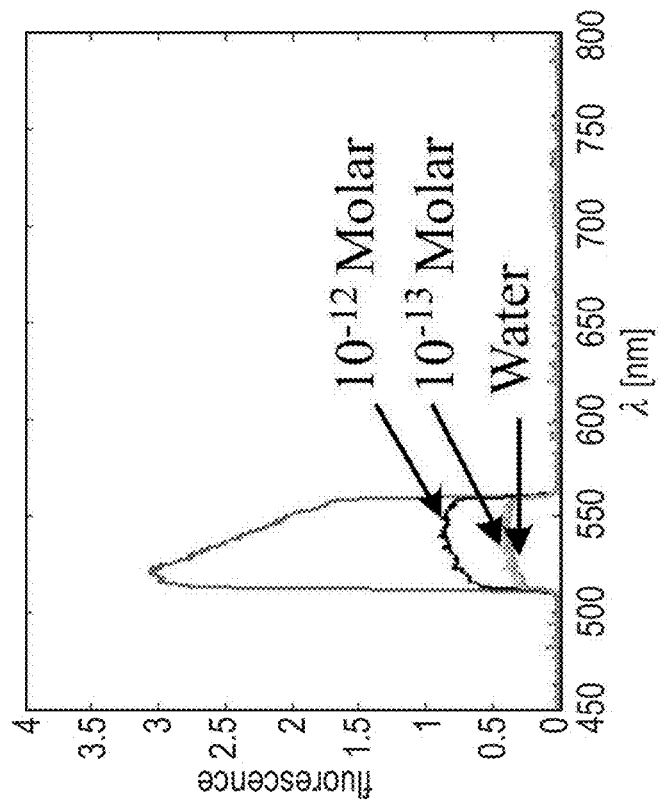

FIGS. 4a and 4b show results from a direct detection experiment of 6-FAM at different concentrations. FIG. 4b shows the excitation laser at 488 nm and several emission spectra of different 6-FAM concentrations. FIG. 4b clearly shows the 585 nm peak of pure water emission spectrum. FIG. 4a depicts the emission spectra confined by spectral filters to the wavelength range of 515-565 nm. Pure water and 1·10$^{-13}$ Molar of 6-FAM results with the same level of emission when the emission wavelength is limited. FIGS. 4*a* and 4*b* demonstrate that limitation of wavelength via spectral filtering to exclude background fluorescence from water is not helpful at target concentrations at or below $10^{-13}$ Molar, although it can be useful at higher concentrations.

As noted above, the modulation motion of the fluorescent dye in and out the orthogonal laser beam produces a regular signal at the PMT (e.g. sinusoidal or other wave form). In an exemplary embodiment of the invention, the regular signal contributes to an improvement in demodulation. The effect of modulation centers the signal at the modulation frequency rather than at DC, in some cases reduces 1/f noise and separates the signal from the background residual fluorescence.

The shot noise limitation of synchronous detection using a Lock-In Amplifier can be calculated assuming 100% modulation of the photo current signal.

Figure 5:
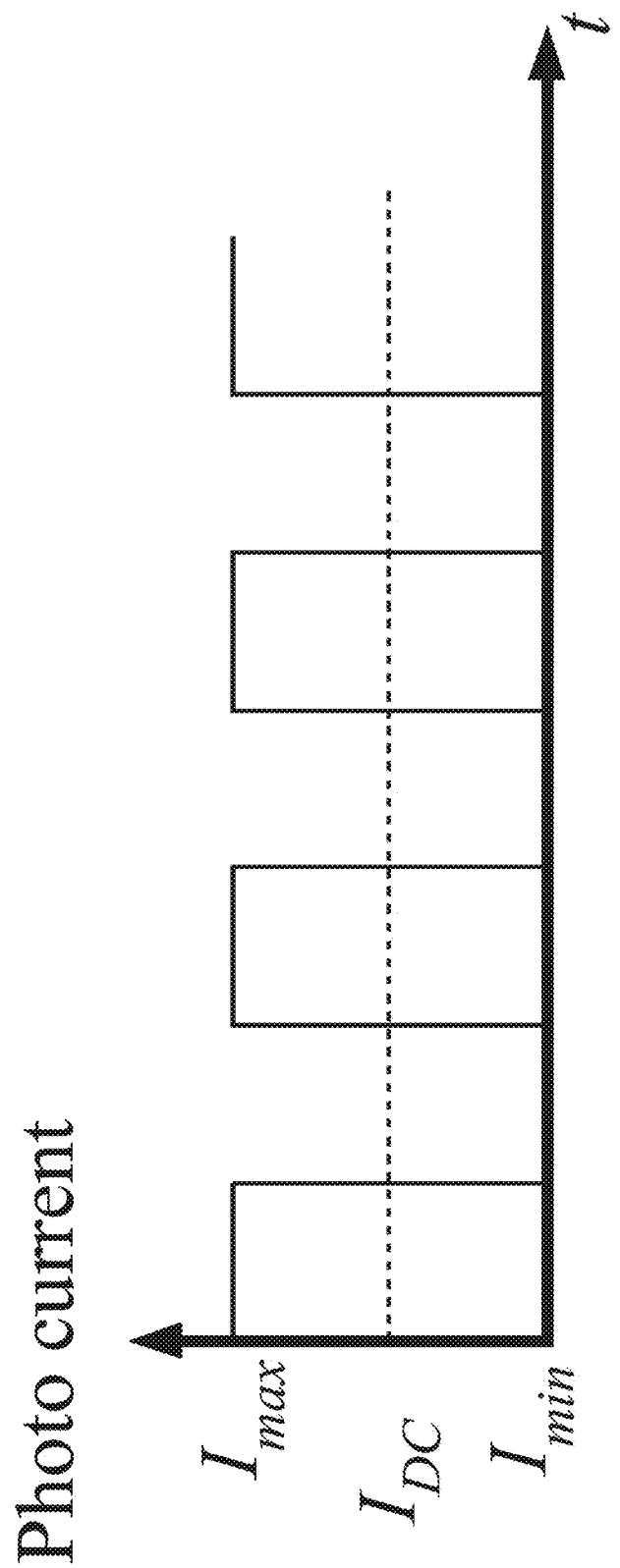
FIG. 5 is a histogram illustrating 100% modulation of a photo current signal over time according to exemplary embodiments of the invention.

In some cases, a maximum value is what is shown in FIG. 5 as DC, but it can depend on implementation. Alternatively, or additionally, a laser excitation beam laser can be aimed at either where probe molecules are expected to be, or where the probe molecules are expected not to be.

As shown in FIG. 5:

The average photocurrent is:

$$I_{DC} = \frac{I_{min} + I_{max}}{2}$$

The shot noise:

$$I_{noise} = \sqrt{2 \cdot e \cdot I_{DC} \cdot B}$$

Where B is the detection bandwidth of the Lock-In Amplifier (B≈1 Hz)

In order to achieve signal to noise ratio of $\sqrt{SNR}=10$, the signal should be:

$$SNR = \frac{I_{DC}}{I_{noise}} = \frac{I_{DC}}{\sqrt{2 \cdot e \cdot I_{DC} \cdot B}} = 10$$

Hence $$I_{DC}^{min} = (10 \cdot \sqrt{2 \cdot e \cdot B})^2 = 200 \cdot 1.6 \cdot 10^{-19} \cdot 1 = 3.2 \cdot 10^{-17} [A]$$

The energy of 520 nm photons (peak emission wavelength of 6-FAM) is:

$$h\upsilon = h \cdot \frac{c}{\lambda} = 6.62 \cdot 10^{-34} \cdot \frac{3 \cdot 10^8}{520 \cdot 10^{-9}} = 3.82 \cdot 10^{-19} [joule]$$

Assuming the PMT has quantum yield of η=0.2, the total rate of photons arriving the PMT is:

$$W = \frac{3.2 \cdot 10^{-17} [A]}{3.82 \cdot 10^{-19} [joule] \cdot 0.2} \cong 420 \left[\frac{photons}{sec}\right]$$

Using a microscope lens (25.4 mm diameter, 16 mm focal length and Numerical Aperture 0.25) to image the detection area to the PMT effective area, the collection efficiency is ~1.5%. Therefore, the total number of photons emitted from the detection area is:

$$\overline{W} = \frac{W}{0.015} = 28,000 \left[\frac{photons}{sec}\right]$$

Given the same laser source (Argon laser model 262A-01, λ=488 nm, output power P=1 mW, beam waist ω=20 μm), The number of molecules required is:

$$N = \frac{\overline{W}}{\phi_F \cdot W} = \frac{28000}{0.9 \cdot 61985} \cong 0.5$$

As noted above, a potential advantage of magnetic modulation is the condensation of all the magnetic beads in a small area where the laser beam is focused on. Hence, assuming a 50 micro litter tube and condensation efficiency of 1% (i.e. only 0.01 of the beads are condensed to the laser beam), a rough estimation of the minimal concentration for synchronous detection (assuming $\sqrt{SNR}=10$) is:

$$C = \frac{N}{V \cdot N_a} = \frac{0.5}{6.02 \cdot 10^{23} \cdot 50 \cdot 10^{-6} \cdot 0.01} \cong 1 \cdot 10^{-18} [Molar]$$

The following experiment was taken in order to demonstrate and visualize the ability of two electromagnetic poles to maneuver small magnetic particles (Dynabeads, M-280, Invitrogen, Carlsbad, Calif.)) in 1-D movement, in and out the laser beam. A 488 nm air cooled argon laser (262A-01 power supply, Spectra-Physics Lasers, Mountain View, Calif.) was used as an excitation light source. The laser beam is directed using a 506 nm long-pass filter (LPF-506-25.222 mm×35.6 mm-HC, CVI Laser, Albukuerque, N. Mex.) into a microscope objective lens (M-10×, 0.25 N.A, 16.5 mm Focal length, Newport Corporation, Irvine, Calif.) which focus the laser beam into a 500 μm wide borosilicate glass tube (RT4905, 0.5×5.0 mm Internal Dimensions, 0.3 mm wall width, Vitrocom, Mountain Lakes, N.J.). The emitted light from the sample is collected using the same microscope objective lens, transmitted through the long-pass filter and detected by a CCD camera (Pl-A741, 1.3 Mega pixels, Pixelink, Ottawa, Canada).

Figure 6:
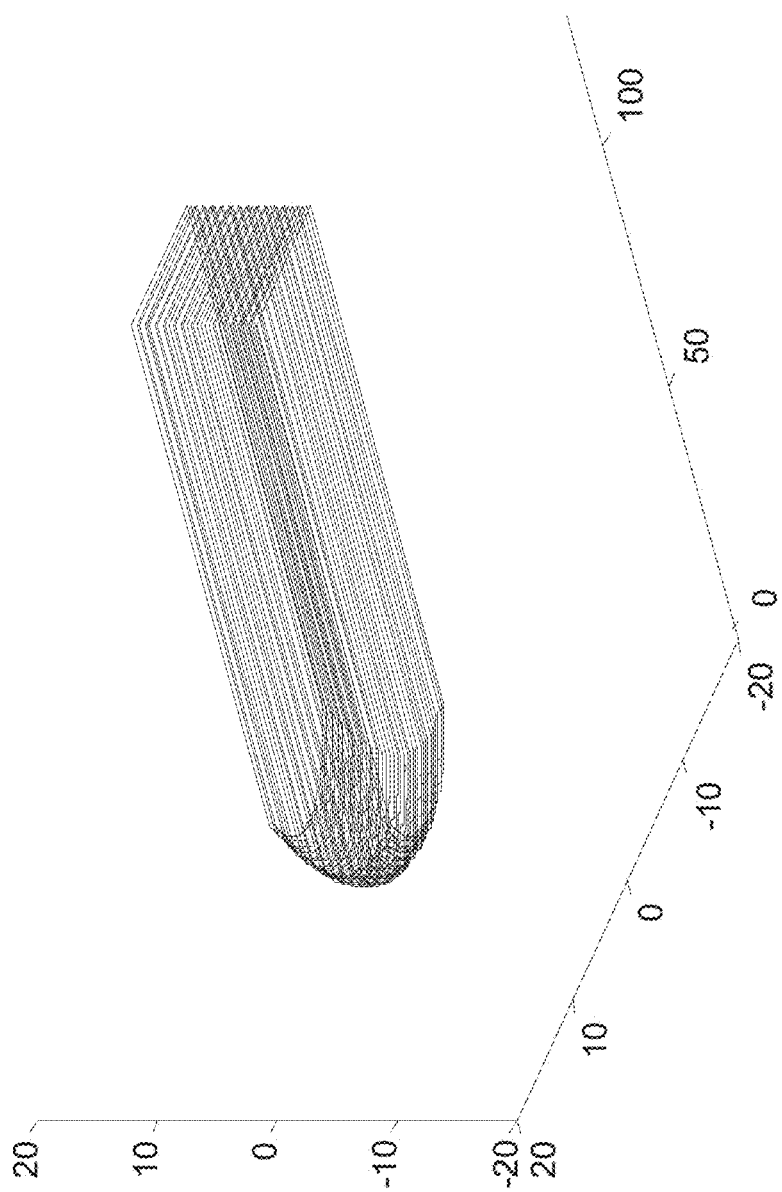
FIG. 6 is a perspective view of an exemplary parabolic tip suitable for use in exemplary embodiments of the invention.

In order to achieve high forces on relatively small magnetic beads, high magnetization saturation material can be used to construct the poles (e.g. M5, 0.3 mm thick, grain oriented silicon steel, 1.9 Tesla). In an exemplary embodiment of the invention, parabolic shaped pole tips contribute to an additional increase in field gradient outside the poles. An exemplary parabolic tip is depicted in FIG. 6. Optionally, two identical 4500 wound coils (wire diameter 0.71 mm) with the poles inside, are placed on an XYZ translation stages (e.g. M-462-XYZ-M, Newport, Irvine, Calif.), one at each side of a rectangular tube.

Figure 7A:
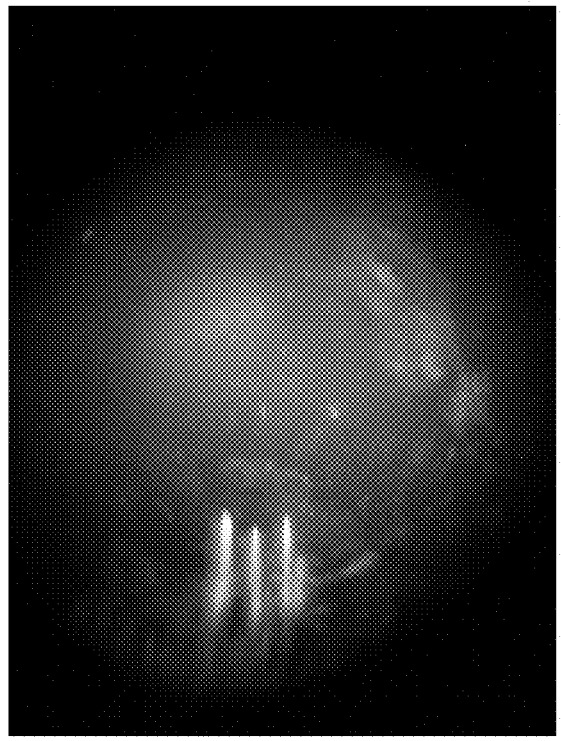
FIGS. 7a and 7b are video still images of fluorescent output signal concentrated using an exemplary embodiment of the invention.
Figure 7B:

FIGS. 7*a* and 7*b* depict results from an experiment in which a sample comprising $2.5 \cdot 10^{-15}$ Molar of small magnetic particles (M-280, Dynabeads) at 50 μlitter Tris-HCl buffer is subject to excitation with a laser beam. The photographs illustrate a sequence of events which occurs as modulation of current applied to the two coils creates a cyclic magnetic field gradient. The cyclic magnetic field gradient initially attracts magnetic beads to one pole (FIG. 7a, left side). As polarity of the magnetic field gradient is reversed, a cloud of condensed magnetic beads cross path of the excitation laser beam (FIG. 7b, center) and eventually pass to the second pole. A periodicity with which the light of FIG. 7b appears will vary with a frequency of cycling of current between the two poles.

For the experiment depicted in FIGS. 7a and 7b current was applied with at 1.35 A with a frequency of 6 Hz. This pair of pictures was made using a probe which was not bound to beads or to a target. An air-cooled argon laser with an excitation wavelength of 488 nm was employed and no quenching system was employed.

In order to apply high forces on relatively small magnetic beads, very high magnetization saturation material is optionally used to construct the poles (M5, 0.3 thick, grain oriented silicon steel, 1.9 Tesla). If a low magnetization saturation material is employed, applied forces will be lower and time for the magnetic field to move the beads will be longer. In embodiments using a low magnetization saturation material, a lower frequency can compensate for the longer time.

Further increase of the field gradient outside the poles is achieved using parabolic shaped pole tips. Two identical 4500 wound coils (0.71 mm wire diameter) with the poles inside, are placed on XYZ translation stages; one at each side of the rectangle tube. In order to maneuver the magnetic beads in a periodic 1-D movement a current modulator which produces successively 1.35 A to each coil at frequencies of 1-6 Hz can optionally be employed. The resulting magnetic field at the poles tips using such an optional configuration was measured to be ~0.7 Tesla.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of detecting at least one target molecule within a population of molecules, the method comprising:
    contacting a plurality of probe molecules, selected to bind specifically with the target molecule, each probe molecule labeled with at least one fluorescent molecule, with the population of molecules containing at least one of said target molecule, where at least one probe molecule binds to at least one target molecule;
    contacting the plurality of probe molecules with magnetic beads, wherein the at least one probe molecule that binds to the target molecule, or a part of that probe molecule, also binds to one of the magnetic beads via an intermediary component;
    forming a cloud of the magnetic beads, condensed;
    illuminating the cloud of magnetic beads with an excitation beam that produces fluorescent emission from the fluorescent molecules labeling the probe molecules or parts of probe molecules bound to the magnetic beads;
    acquiring a background signal and a signal of the fluorescent emission;
    detecting the fluorescent emission signal over the background signal; and
    determining from the detected fluorescent emission signal, one or both of a presence of the target molecule within the population of molecules, and an amount of the target molecules within the population of molecules;
    wherein the method is an energy transfer-based assay, wherein at least one of the probe molecules includes a probe molecule labeled with at least one or more fluorescent molecules at a first end thereof and having one or more quenching molecules at a second end thereof; and
    wherein, prior to detecting the fluorescent signal, the one or more fluorescent molecules are separated from the one or more quenching molecules.

2. The method according to claim 1, wherein said contacting a plurality of probe molecules with the population of molecules potentially containing at least one of said target molecule includes at least one probe molecule selectively binding to at least one target molecule.

3. The method according to claim 1, wherein said contacting the plurality of probe molecules with magnetic beads includes at least one magnetic bead selectively binding with a probe molecule via at least one intermediary component.

4. The method according to claim 1, wherein the intermediary component is one or more of the following: biotin, a DNA sequence, an RNA sequence, an antibody, a protein, and a target molecule.

5. The method according to claim 1, wherein the at least one probe molecule binds with the target molecule before the magnetic bead binds with the probe molecule or part of the probe molecule via an intermediary component.

6. The method according to claim 1, wherein the at least one probe molecule binds with the target molecule after the magnetic bead binds with the probe molecule or part of the probe molecule via an intermediary component.

7. The method of claim 1, wherein the one or more fluorescent molecules are separated from the one or more quencher molecules by PCR (polymerase chain reaction).

8. The method according to claim 1, wherein the method is a sandwich-based assay, wherein a capture probe, labeled with a portion of the intermediary component, and a signaling probe, labeled with a fluorescent molecule, hybridize to the target molecule.

9. The method of claim 1, wherein the fluorescent signal is detected by a CCD camera.

10. The method according to claim 1, wherein said at least one target molecule includes at least one molecule type selected from the group consisting of a nucleic acid sequence, an amino acid sequence, a carbohydrate, a carbohydrate sequence, an ion, and a feature of a protein determined by non-primary structure.

11. The method according to claim 1, wherein at least some of said plurality of probe molecules include at least one of nucleic acids, peptides, proteins, antibodies, and ion chelators; and wherein at least some of said plurality of target molecules include at least one molecule type selected from the group consisting of a nucleic acid sequence, an amino acid sequence, a carbohydrate, a carbohydrate sequence, an ion, and a feature of a protein determined by non-primary structure.

12. The method according to claim 1, wherein said at least one probe molecule bound to said at least one target molecule includes at least one protein molecule bound to one protein target.

13. The method according to claim 1, wherein said at least one probe molecule bound to said at least one target molecule includes at least one nucleic acid molecule bound to a nucleic acid target.

14. The method according to claim 1, wherein said at least one probe molecule bound to said at least one target molecule includes at least one antibody bound to an epitope.

15. The method according to claim 1, wherein the intermediary component through which the probe molecule or part of the probe molecule binds to one of the magnetic beads does not comprise any part of the target molecule.

16. The method according to claim 1 wherein at least a first portion of said plurality of probe molecules each have a fluorescent label and are bound to a target and wherein at least a second portion of said probe molecules are each attached to a magnetic bead and are bound to the same target.

17. The method according to claim 16, wherein the probe molecules bound to the target molecules include at least one protein molecule bound to one protein target.

18. The method according to claim 16, wherein the probe molecules bound to the target molecules include at least one nucleic acid molecule bound to a nucleic acid target.

* * * * *